(12) United States Patent
Yoshida et al.

(10) Patent No.: US 11,857,167 B2
(45) Date of Patent: Jan. 2, 2024

(54) IMAGE PICKUP UNIT AND ENDOSCOPE

(71) Applicant: OLYMPUS CORPORATION, Tokyo (JP)

(72) Inventors: Kyosuke Yoshida, Kokubunji (JP); Toshiyuki Fujii, Machida (JP); Shun Ogi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 408 days.

(21) Appl. No.: 17/186,823

(22) Filed: Feb. 26, 2021

(65) Prior Publication Data

US 2021/0275005 A1    Sep. 9, 2021

Related U.S. Application Data

(63) Continuation of application No. PCT/JP2019/004480, filed on Feb. 7, 2019.

(30) Foreign Application Priority Data

Aug. 28, 2018  (JP) .................................. 2018-159357

(51) Int. Cl.
*A61B 1/05*     (2006.01)
*A61B 1/00*     (2006.01)
(Continued)

(52) U.S. Cl.
CPC .......... *A61B 1/051* (2013.01); *A61B 1/00124* (2013.01); *A61B 1/07* (2013.01);
(Continued)

(58) Field of Classification Search
CPC ....... A61B 1/051; A61B 1/00124; A61B 1/07; A61B 1/00096; G02B 23/2469;
(Continued)

(56) References Cited

U.S. PATENT DOCUMENTS

2013/0303853 A1* 11/2013 Takahashi .......... G02B 23/2476
                                                    600/134
2015/0293343 A1* 10/2015 Nagase .............. G02B 23/2484
                                                    348/76

FOREIGN PATENT DOCUMENTS

EP           2674095 A1    12/2013
JP      H06-153095 A        5/1994
(Continued)

OTHER PUBLICATIONS

International Search Report dated Apr. 23, 2019 issued in PCT/JP2019/004480.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An image pickup unit includes: a metal barrel holding an objective lens; a substrate barrel formed of a circuit formed product having insulation property; an image sensor having a chip size package; plural electrodes formed in a penetrating manner from an inside of a substrate barrel to a proximal end side in an exposed manner, the plural electrodes being electrically connected to an image sensor in the substrate barrel; an electric conductive portion formed on an outer surface of the substrate barrel, having an insulation property with respect to the metal barrel, and having a predetermined creepage distance by which a current such as static electricity can be discharged; a ground electrode electrically connected to the electric conductive portion; and a cable provided with plural wires connected to a ground wire connected to the ground electrode and plural wires connected to the plural electrodes.

21 Claims, 13 Drawing Sheets

(51) Int. Cl.
   *A61B 1/07*    (2006.01)
   *G02B 23/24*   (2006.01)
   *H04N 23/55*   (2023.01)
   *H04N 23/50*   (2023.01)

(52) U.S. Cl.
   CPC ..... *G02B 23/2469* (2013.01); *G02B 23/2484* (2013.01); *H04N 23/55* (2023.01); *H04N 23/555* (2023.01)

(58) Field of Classification Search
   CPC .. G02B 23/2484; H04N 23/55; H04N 23/555; H04N 7/18
   See application file for complete search history.

(56) References Cited

FOREIGN PATENT DOCUMENTS

| | | | |
|---|---|---|---|
| JP | 2000-60793 A | | 2/2000 |
| JP | 2000060793 A | * | 2/2000 |
| JP | 2001-128937 A | | 5/2001 |
| JP | 2007-89888 A | | 4/2007 |
| JP | 2008-130738 A | | 6/2008 |
| JP | 2009-201762 A | | 9/2009 |
| JP | 2019-25207 A | | 2/2019 |
| WO | WO 2013/084548 A1 | | 6/2013 |
| WO | WO 2017/130886 A1 | | 8/2017 |

\* cited by examiner

IMAGE PICKUP UNIT AND ENDOSCOPE

CROSS REFERENCE TO RELATED APPLICATION

This application is a continuation application of PCT/JP2019/004480 filed on Feb. 7, 2019 and claims benefit of Japanese Application No. 2018-159357 filed in Japan on Aug. 28, 2018, the entire contents of which are incorporated herein by this reference.

BACKGROUND OF THE INVENTION

1. Field of the Invention

The present invention relates to an image pickup unit for endoscope disposed in a frame made of metal, and an endoscope which includes the image pickup unit.

2. Description of the Related Art

In recent years, endoscopes have been popularly used in a medical field and an industrial field. With respect to such endoscopes, there have been known an endoscope where an elongated insertion section is inserted into a flexible body cavity, and an endoscope for surgery which is inserted into a rigid body cavity.

In such an endoscope, an image pickup unit equipped with an image sensor disclosed in, for example, Japanese Patent Application Laid-Open Publication No. 6-153095 or Japanese Patent Application Laid-Open Publication No. 2000-60793 is incorporated in a distal end portion of an insertion section.

SUMMARY OF THE INVENTION

According to an aspect of the present invention, there is provided an image pickup unit which includes: a metal barrel disposed on a distal end side of the image pickup unit and holding an objective lens; a substrate barrel having a case shape, the substrate barrel being fitted to a proximal end side of the metal barrel, the substrate barrel being formed of a circuit formed product having insulation property; an image sensor disposed in the substrate barrel; a plurality of electrodes formed in a penetrating manner from an inside of the substrate barrel to a proximal end side in an exposed manner, the plurality of electrodes being electrically connected to the image sensor in the substrate barrel; an electric conductive member formed on an outer surface of the substrate barrel, the electric conductive member having a predetermined creepage distance with respect to the metal barrel in a state where the substrate barrel and the metal barrel are fitted to each other; a ground electrode that is one of the plurality of electrodes and electrically connected to the electric conductive member; a cable including a ground wire connected to the ground electrode and a plurality of wires connected to the plurality of electrodes; and a convex portion extending toward a proximal end side of the metal barrel, the convex portion being disposed on the substrate barrel having the predetermined creepage distance with respect to the electric conductive member, wherein the electric conductive member has a predetermined length where the electric conductive member overlaps with the convex portion in a range where the metal barrel is adjusted so that the image pickup unit satisfies a predetermined optical performance.

According to another aspect of the present invention, there is provided an endoscope where a distal end portion equipped with an exterior barrel made of metal in which an image pickup unit is incorporated is disposed in an insertion section, wherein the image pickup unit includes: a metal barrel holding an objective lens; a substrate barrel having a case shape, the substrate barrel being disposed on and fitted to a proximal end side of the metal barrel, the substrate barrel being formed of a circuit formed product having insulation property; an image sensor disposed in the substrate barrel; a plurality of electrodes formed in a penetrating manner from an inside of the substrate barrel to a proximal end side in an exposed manner, the plurality of electrodes being electrically connected to the image sensor; an electric conductive member formed on an outer surface of the substrate barrel, the electric conductive member having a predetermined creepage distance with respect to the metal barrel in a state where the substrate barrel and the metal barrel are fitted to each other; a ground electrode that is one of the plurality of electrodes and electrically connected to the electric conductive member; a cable including a ground wire connected to the ground electrode and a plurality of wires connected to the plurality of electrodes; and a convex portion extending toward a proximal end side of the metal barrel, the convex portion being disposed on the substrate barrel having the predetermined creepage distance with respect to the electric conductive member, wherein the electric conductive member has a predetermined length so as to overlap the convex portion within a range where the metal barrel is adjusted so that the image pickup unit satisfies a predetermined optical performance.

DETAILED DESCRIPTION OF THE PREFERRED EMBODIMENTS

Hereinafter, the present invention is described with reference to drawings.

In the description made hereinafter, drawings based on the following embodiment are schematic views. Accordingly, note that a relationship between a thickness and a width of each portion, a ratio between thicknesses of respective portions and the like differ from the corresponding relationships of portions of an actual image pickup unit and an endoscope. There may be a case where portions of the actual image pickup unit and the endoscope are described with different size relationship or different ratios between the drawings.

First, an endoscope according to a mode of an embodiment of the present invention is described hereinafter with reference to drawings. Although the description is made hereinafter by exemplifying a rigid endoscope where an insertion section is rigid, the present invention is not limited to such a case, and is a technique also applicable to a flexible endoscope where an insertion section is formed of a flexible tube.

The endoscope according to a mode of the present invention is described.

Figure 1:
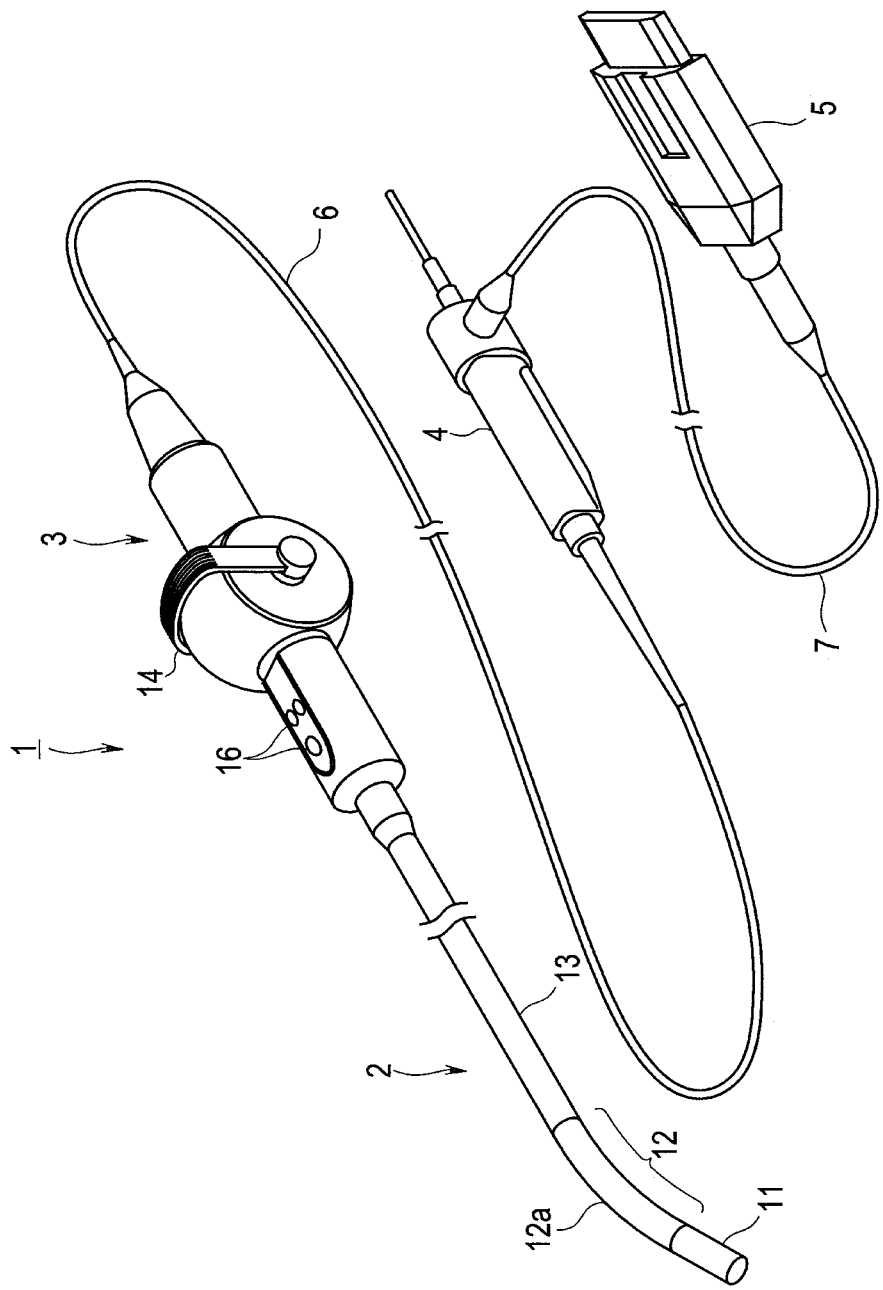
FIG. 1 is a perspective view showing an overall configuration of an endoscope according to a mode of a first embodiment of the present invention.
Figure 2:
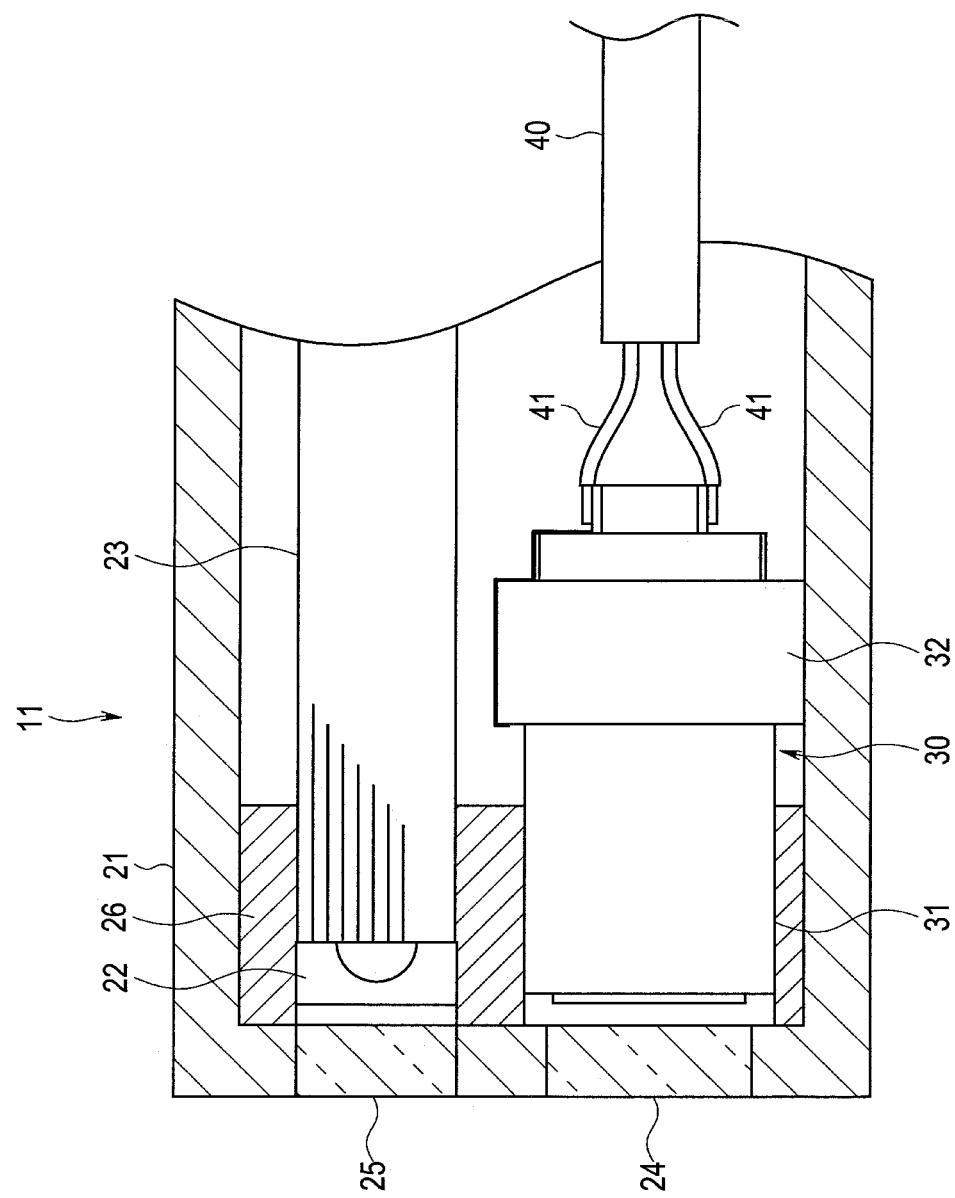
FIG. 2 is a cross-sectional view showing an inside of a distal end portion of an insertion section of the endoscope.
Figure 3:
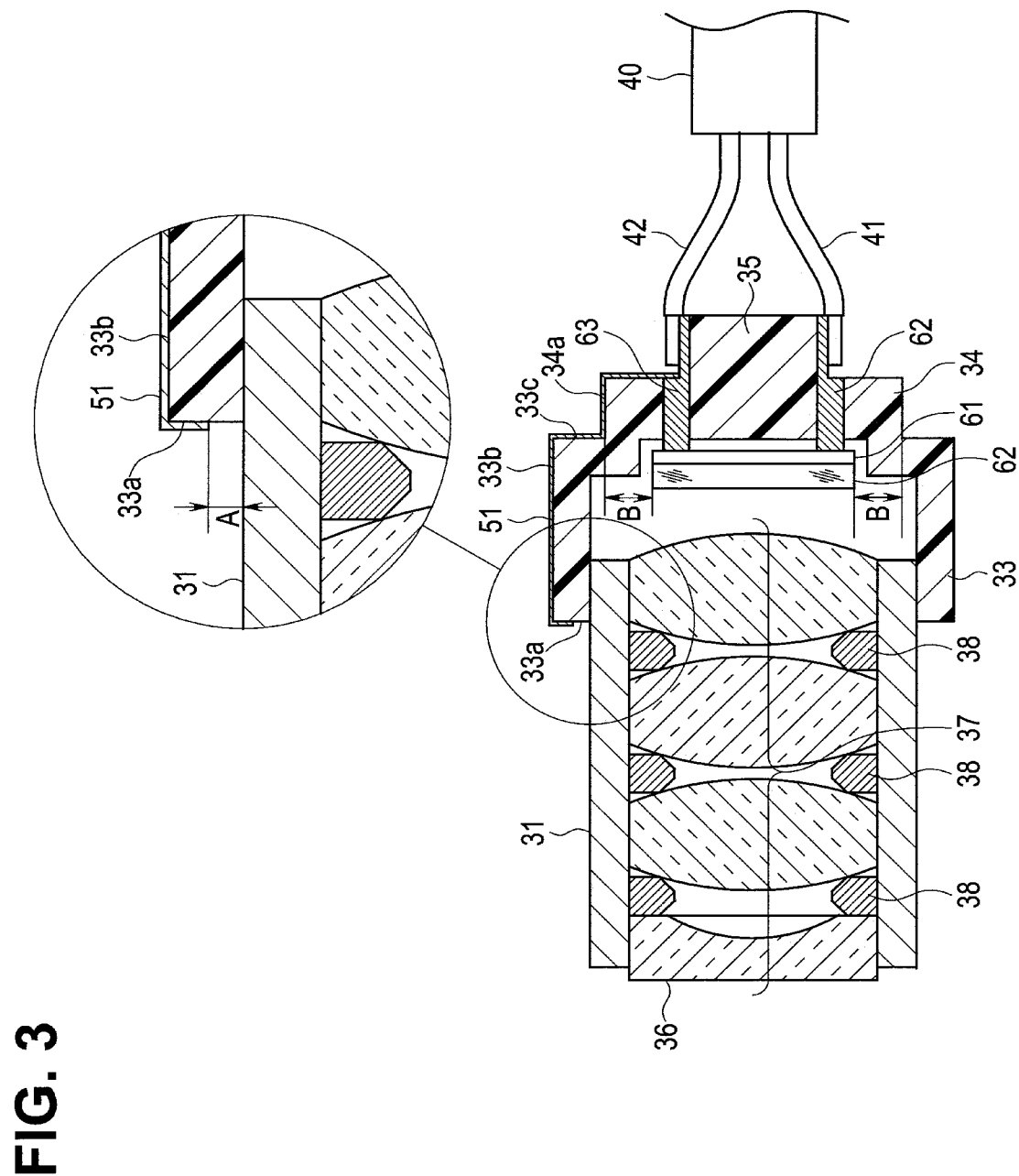
FIG. 3 is a cross-sectional view showing a configuration of an image pickup unit of the endoscope.
Figure 4:
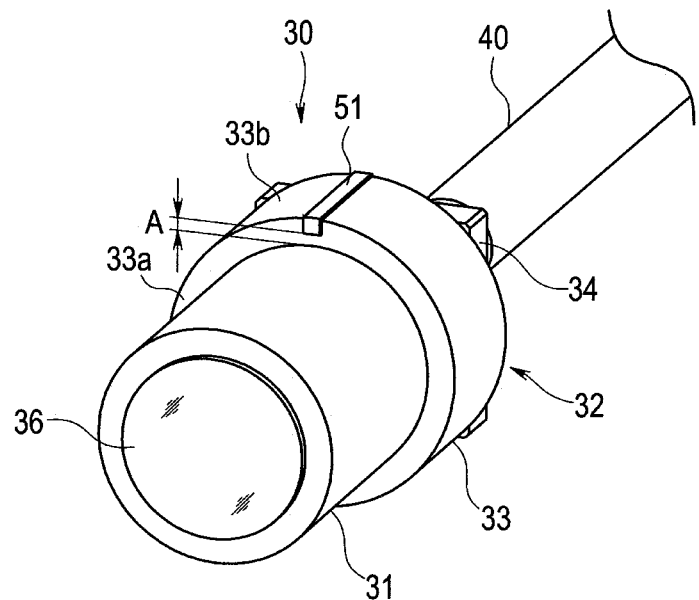
FIG. 4 is a perspective view of the image pickup unit of the endoscope as viewed from a distal end side.
Figure 5:
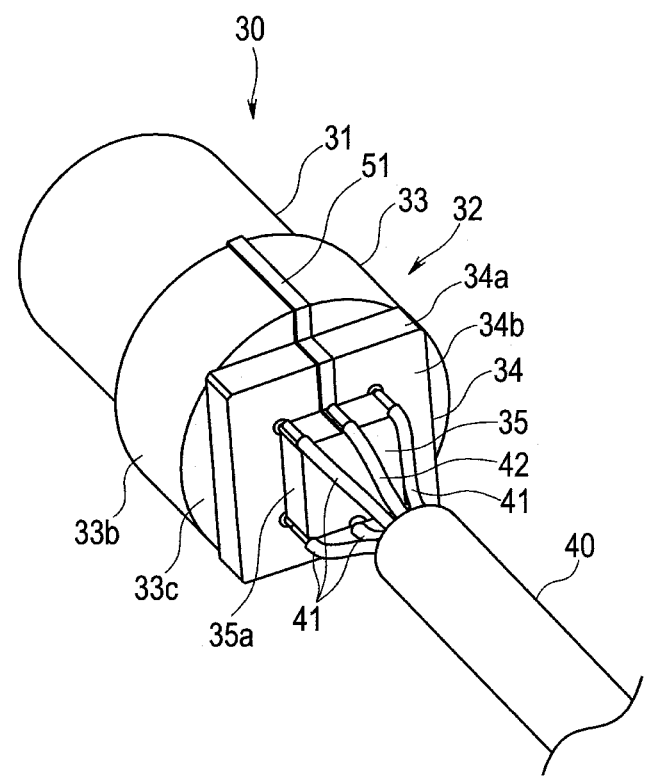
FIG. 5 is a perspective view of the image pickup unit of the endoscope as viewed from a proximal end side.
Figure 6:
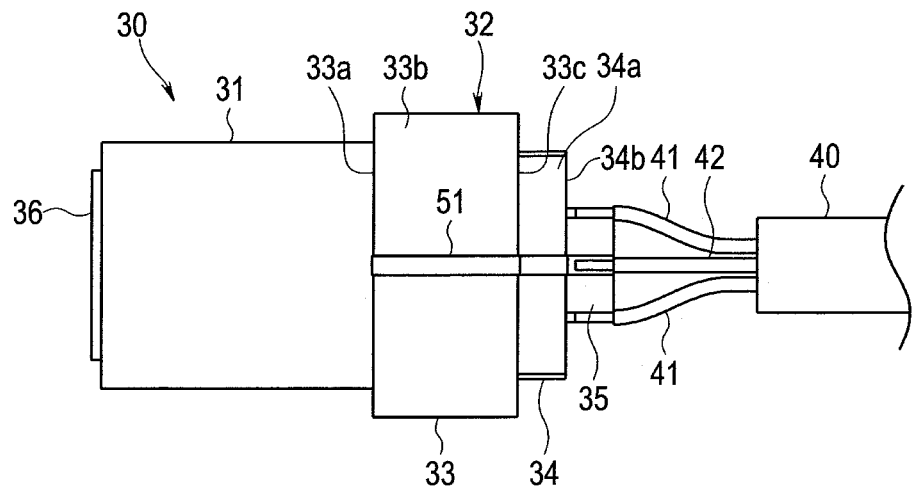
FIG. 6 is a top plan view showing a configuration of the image pickup unit of the endoscope.
Figure 7:
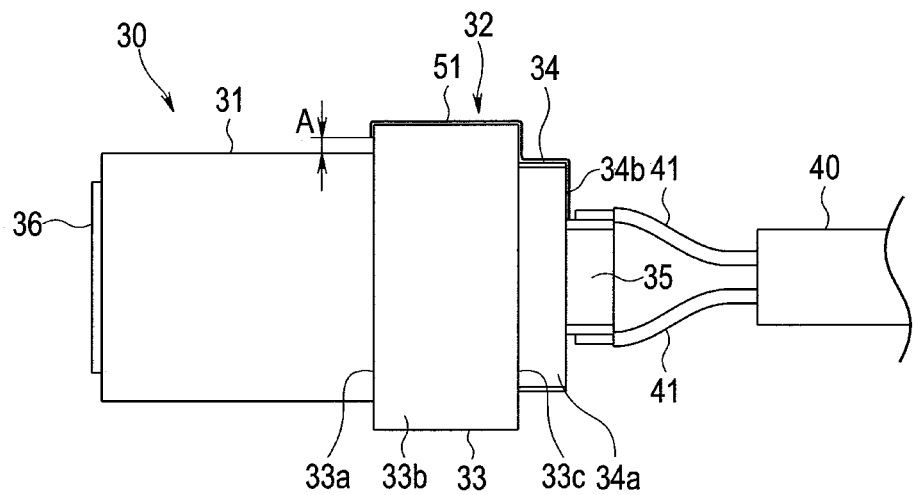
FIG. 7 is a left side view of the configuration of the image pickup unit of the endoscope.
Figure 8:
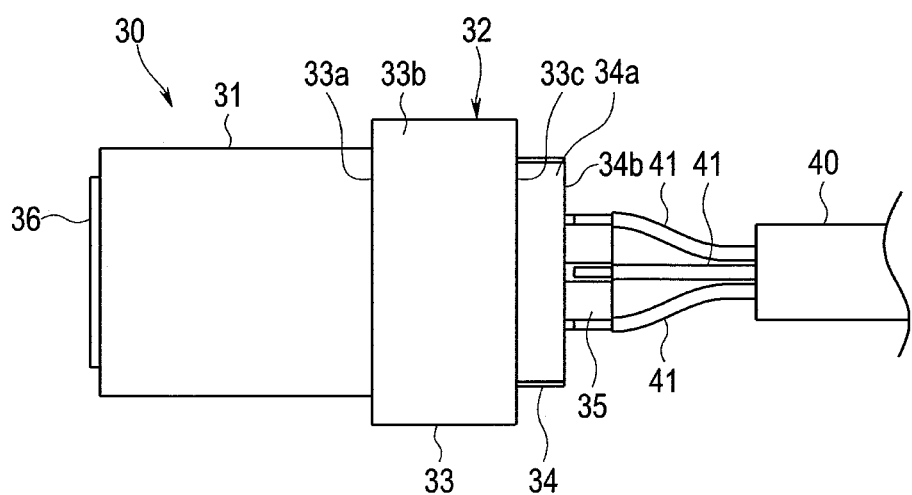
FIG. 8 is a bottom plan view showing the configuration of the image pickup unit of the endoscope.
Figure 9:
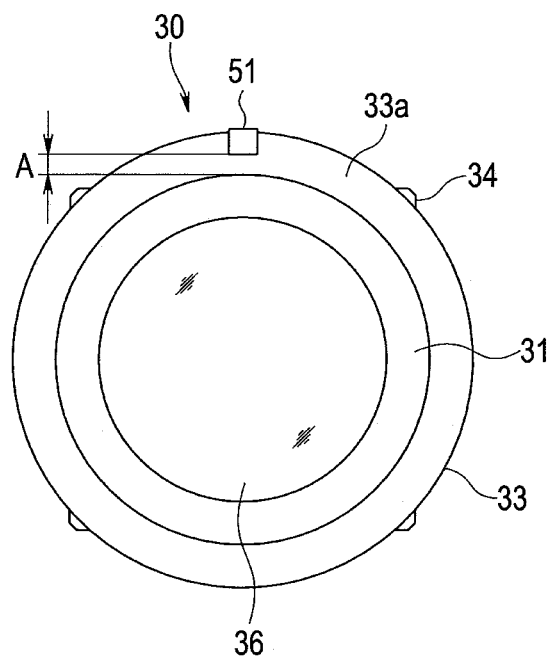
FIG. 9 is a front view showing the configuration of the image pickup unit of the endoscope.
Figure 10:
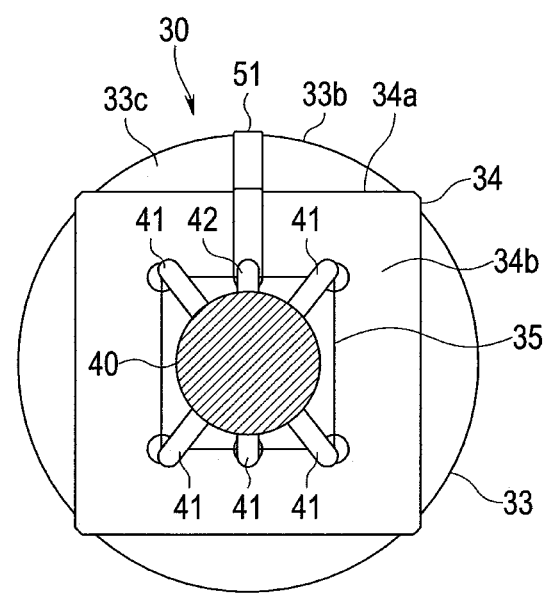
FIG. 10 is a back view showing the configuration of the image pickup unit of the endoscope.
Figure 11:
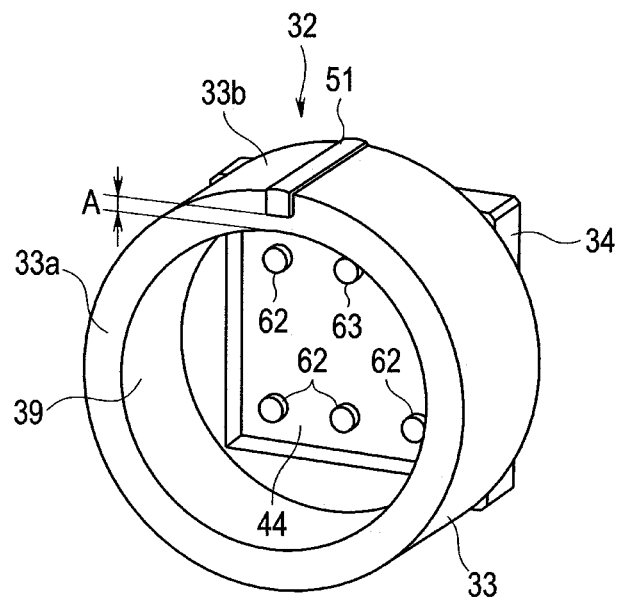
FIG. 11 is a perspective view of a substrate barrel of the endoscope as viewed from a distal end side.
Figure 12:
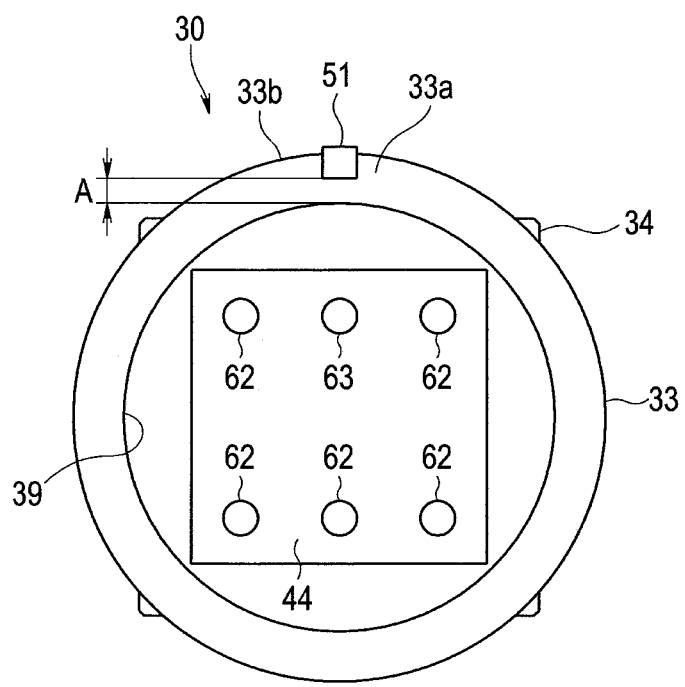
FIG. 12 is a front view showing a configuration of the substrate barrel of the endoscope.
Figure 13:
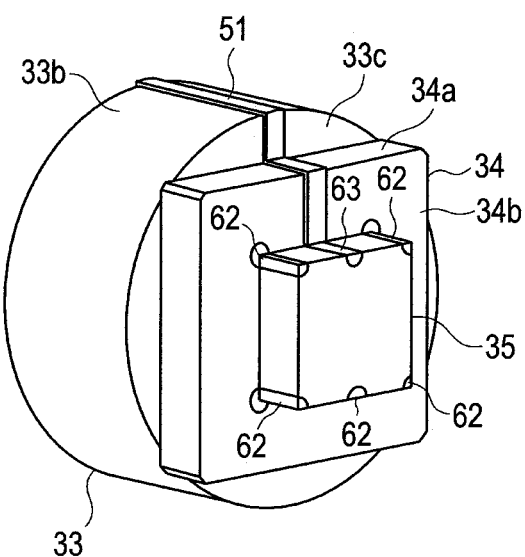
FIG. 13 is a perspective view of the substrate barrel of the endoscope as viewed from a proximal end side.
Figure 14:
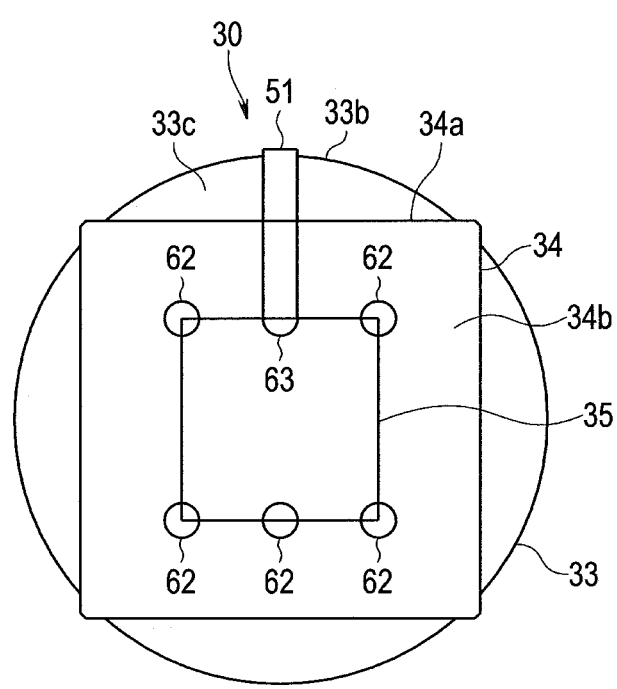
FIG. 14 is a back view showing the configuration of the substrate barrel of the endoscope.
Figure 15:
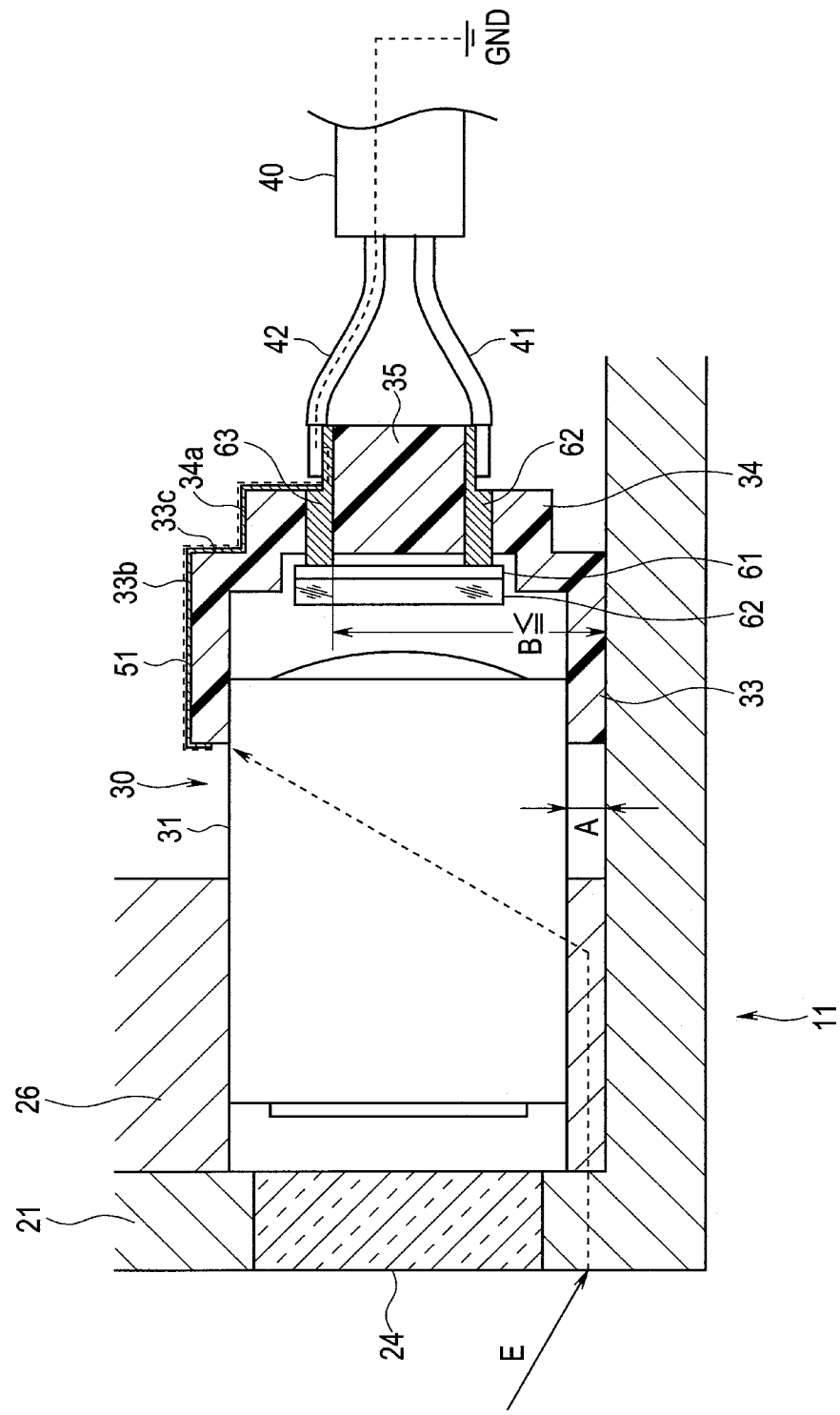
FIG. 15 is a partial cross-sectional view of a distal end portion on which the image pickup unit is mounted provided for describing a state where a current such as a high frequency current or static electricity is applied in the endoscope.

FIG. 1 is a perspective view showing an overall configuration of the endoscope. FIG. 2 is a cross-sectional view showing an inside of a distal end portion of an insertion section. FIG. 3 is a cross-sectional view showing a configuration of an image pickup unit. FIG. 4 is a perspective view of the image pickup unit as viewed from a distal end side. FIG. 5 is a perspective view of the image pickup unit as viewed from a proximal end side. FIG. 6 is a top plan view showing a configuration of the image pickup unit. FIG. 7 is a left side view of the configuration of the image pickup unit. FIG. 8 is a bottom plan view showing the configuration of the image pickup unit. FIG. 9 is a front view showing the configuration of the image pickup unit. FIG. 10 is a back view showing the configuration of the image pickup unit. FIG. 11 is a perspective view of a substrate barrel as viewed from a distal end side. FIG. 12 is a front view showing a configuration of the substrate barrel. FIG. 13 is a perspective view of the substrate barrel as viewed from a proximal end side. FIG. 14 is a back view showing the configuration of the substrate barrel. FIG. 15 is a partial cross-sectional view of a distal end portion on which the image pickup unit is mounted provided for describing a state where a current such as a high frequency current or static electricity is applied.

As shown in FIG. 1, an endoscope 1 mainly includes a long insertion section 2, an operation section 3 connected to a proximal end of the insertion section 2, a light guide connector 4 connected to a light source device not shown, and a video connector 5 connected to a video system center not shown.

In the endoscope 1, the operation section 3 and the light guide connector 4 are connected to each other via a flexible cable 6 as a universal cord, and the light guide connector 4 and the video connector 5 are connected to each other via a communication cable 7.

The insertion section 2 is formed by mainly connecting a distal end portion 11 formed of a metal member made of stainless steel or the like, a bending portion 12 and a rigid tube 13 formed of a metal tube made of stainless steel or the like in this order. The insertion section 2 forms a portion inserted into a body. Cables which supply a power source and allow communication using control signals such as image pickup signals, a light guide which guides an illumination light and the like are incorporated in the insertion section 2.

In the operation section 3, an angle lever 14 as a bending operation member for operating the bending portion 12 by a remote control and various switches 16 which operate a light source device (not shown), a video system center (not shown) and the like are disposed. The angle lever 14 is bending operation means which can operate the bending portion 12 of the insertion section 2 in two directions, that is, upward and downward directions. The operation section 3 may include two angle levers 14 so that the bending portion 12 is bendable in four directions, that is, upward, downward, leftward, and rightward directions.

The bending portion 12 of the insertion section 2 includes a bending tube not shown. The bending tube is bendably operated by bending operation wires (not shown) which are towed or slackened by the angle lever 14. The bending portion 12 includes a bending rubber 12a which covers the bending tube as an outer skin.

The distal end portion 11 of the insertion section 2 includes a distal end barrel 26 made of metal such as stainless steel which fits in an exterior barrel 21 formed using metal such as stainless steel. An image pickup unit 30, and a light guide 23 where an illumination lens 22 which is an illumination optical system is disposed on a distal end of the light guide 23 are inserted into and fixed to the distal end barrel 26. An observation window 24 and an illumination window 25 made of glass, a transparent resin or the like are disposed on a distal end surface of the exterior barrel 21.

The configuration of the image pickup unit 30 according to the embodiment is described in detail.

As shown in FIG. 3 to FIG. 10, the image pickup unit 30 includes: a lens hold barrel 31 which is disposed on a distal end side of the image pickup unit 30, and is a cylindrical metal barrel formed using metal such as stainless steel; and a substrate barrel 32 which is connected to a proximal end of the lens hold barrel 31, in which an image sensor is disposed, and which has insulation property.

An objective lens group 37 including an objective lens 36 disposed on a most distal end is held in the lens hold barrel 31. A plurality of spacer tubes 38 which adjust distances in the objective lens group 37 are disposed in the lens hold barrel 31.

The lens hold barrel 31 is inserted into the substrate barrel 32, and fixed to the substrate barrel 32 by an adhesive agent or the like at an adjustment position where the image pickup unit 30 satisfies a predetermined optical performance.

In the substrate barrel 32, an image sensor 61 which is a tip size package (CSP) and receives an optical image is disposed. A cover glass 62 is disposed on a surface of the image sensor 61. The image sensor 61 is connected to a plurality of electrodes 62 and a ground (GND) electrode 63 which are formed in the substrate barrel 32 in a penetrating manner.

In the embodiment, the substrate barrel 32 is a case-shaped substrate which is formed of a molded interconnect device (MID) (also referred to as a circuit formed product, a stereoscopic circuit part). The substrate barrel 32 is not limited to a circuit formed product, but may be a product where wires, through holes, terminal portions and the like are mounted on an insulation barrel formed using a resin, ceramic, glass or the like.

The substrate barrel 32 may be formed such that a cutout is formed in a portion of a side wall.

The substrate barrel 32 includes: a cylindrical portion 33 to which the lens hold barrel 31 is bonded; a rectangular barrel portion 34 having a block shape formed on a proximal end of the cylindrical portion 33; and a wiring portion 35 having a rectangular block shape formed on a proximal end of the rectangular barrel portion 34.

A metal PAD portion 51 which forms an electric conductive path is continuously formed as a pattern on the substrate barrel 32 covering a distal end surface 33a of the cylindrical portion 33, a side surface 33b and a proximal end surface 33c forming an outer peripheral surface, and one side surface 34a and a proximal end surface 34b of the rectangular barrel portion 34. The metal PAD portion 51 is formed on a surface of the substrate barrel 32, and a thickness of the metal PAD portion 51 in an outer diameter direction is approximately a plating thickness.

The metal PAD portion 51 is formed in a spaced-apart manner from the lens hold barrel 31 with a predetermined creepage distance A on the distal end surface 33a of the cylindrical portion 33 (see FIG. 3, FIG. 4, FIG. 7, FIG. 9 and the like). In other words, the metal PAD portion 51 is electrically non-conductive with the lens hold barrel 31 made of metal.

The predetermined creepage distance A is a distance which ensures insulation property between the metal PAD portion 51 and the lens hold barrel 31, and enables discharging of a current such as a leak current or static electricity from a high frequency treatment instrument or the like used together with the endoscope 1 between the metal PAD portion 51 and the lens hold barrel 31.

The metal PAD portion 51 is electrically connected to the GND electrode 63 formed on the wiring portion 35 of the substrate barrel 32 (see FIG. 3).

The plurality of electrodes 62 and the GND electrode 63 are formed on the wiring portion 35 of the substrate barrel 32 in an exposed manner. In the wiring portion 35, a plurality of wires 41 and a ground wire 42 of the cable 40 are connected to the plurality of electrodes 62 or the GND electrode 63.

An adhesive agent, a resin agent or the like not shown covers a periphery of the image pickup unit 30 and is solidified so as to reinforce connecting portions between the wiring portion 35 of the substrate barrel 32 and the wires 41 and the ground wires 42 of the cable 40.

The image pickup unit 30 ensures mechanical durability by disposing the image sensor 61 in the substrate barrel 32.

As shown in FIG. 11 and FIG. 12, an opening portion 39 having circular cross section is formed in the substrate barrel 32 on a distal end side of the cylindrical portion 33. The lens hold barrel 31 is inserted into the opening portion 39, is optically positioned, and is fixed.

In the embodiment, in the substrate barrel 32, a plurality of electrodes, i.e., five electrodes 62 and one GND electrode 63 protrude from an inner wall surface 44 which forms a bottom portion in the cylindrical portion 33. The inner wall surface 44 forms a surface approximately perpendicular to a photographing optical axis.

Five electrodes 62 and one GND electrode 63 which protrude from the inner wall surface 44 are electrically connected to terminals of the image sensor 61 when the image sensor 61 is mounted on the substrate barrel 32.

The image sensor 61 is disposed in the substrate barrel 32 with a predetermined insulation distance B provided between the image sensor 61 and the metal PAD portion 51 formed on an outer surface of the substrate barrel 32 (see FIG. 3).

By providing the predetermined insulation distance B in this manner, even when a current such as a high-frequency leak current or static electricity is discharged to the metal PAD portion 51, a current from the outside is not applied to the image sensor 61. Further, discharging of a current from the image sensor 61 to the metal PAD portion 51 is also prevented.

Five electrodes 62 and the GND electrode 63 are formed such that the electrodes penetrate into the rectangular barrel portion 34 through the inner wall surface 44. As shown in FIG. 13 and FIG. 14, the electrodes 62 and the GND electrode 63 extend to be exposed at four corners of the wiring portion 35 and at centers of upper and lower portions of the wiring portion 35.

As described above, the plurality of wires 41 and the ground wire 42 of the cable 40 are electrically connected by soldering or the like to five electrodes 62 and the GND electrode 63 exposed on the wiring portion 35.

The GND electrode 63 is disposed at the center of the upper portion of the wiring portion 35, and the metal PAD portion 51 is electrically connected to the GND electrode 63. Further, the ground wire 42 of the cable 40 is connected to the GND electrode 63.

The ground wire 42 of the cable 40 is connected to a patient GND. In other words, the metal PAD portion 51 is electrically connected to the patient GND by the ground wire 42 connected to the GND electrode 63.

In the image pickup unit 30 having the above-mentioned configuration, as shown in FIG. 15, there may be a case where in a state where the image pickup unit 30 is mounted on the distal end portion 11 of the endoscope 1, a current E from the outside such as a leak current from a high frequency treatment instrument used together with the endoscope 1 or static electricity is applied to the exterior barrel 21 made of metal, and the current E flows into the lens hold barrel 31 made of metal through the distal end barrel 26.

In this case, the current E which flows into the lens hold barrel 31 of the image pickup unit 30 is discharged to the metal PAD portion 51 of the substrate barrel 32 from the lens hold barrel 31, flows into the metal PAD portion 51 and the GND electrode 63, and eventually flows into the patient GND from the ground wire 42 connected to the GND electrode 63.

In this manner, the image pickup unit 30 is configured such that the metal PAD portion 51 which is a conductive path provided as a countermeasure for leaked electricity and static electricity is formed on an outer peripheral surface of the substrate barrel 32 which is formed on the lens hold barrel 31 made of metal by an insulation material, and the metal PAD portion 51 is electrically connected to the ground wire 42.

Accordingly, conventionally, the image pickup unit 30 requires a reinforcing barrel made of metal or the like around the image pickup unit 30 for ensuring mechanical durability. However, in this embodiment, the image pickup unit 30 is configured such that mechanical durability is ensured by disposing the image sensor 61 in the substrate barrel 32, and it is possible to prevent an excessively large current E such as a leak current from a high frequency treatment instrument or the like, or static electricity from flowing into the image sensor 61.

With such a configuration, compared to the prior art, in the image pickup unit 30, a reinforcing barrel, a jumper wire and the like become unnecessary and hence, the number of parts can be reduced whereby assembling property of the image pickup unit 30 can be enhanced. Further, the reduction in the number of parts enables miniaturization of the image pickup unit 30.

As has been described above, the image pickup unit 30 according to the embodiment has an advantage that the image pickup unit 30 contributes to the miniaturization of the distal end portion 11 of the insertion section 2 of the endoscope 1.

In mounting the image pickup unit 30 on the distal end portion 11 of the insertion section 2, the GND electrode 63 mounted on the substrate barrel 32 is fixed to the distal end barrel 26 such that the predetermined insulation distance B or more (B is provided from the exterior barrel 21 made of metal (see FIG. 15).

The image pickup unit 30 is mounted on the distal end portion 11 such that the distance between the inner surface of the exterior barrel 21 and the outer surface of the lens hold barrel 31 has a predetermined creepage distance A which ensures insulation property, and can discharge a current E such as a leak current from high frequency treatment instrument or the like or static electricity between the metal PAD portion 51 and the exterior barrel 21.

In the image pickup unit 30, the substrate barrel 32 is formed of an insulation member and hence, the image pickup unit 30 can be disposed in the distal end portion 11 even in a state where the substrate barrel 32 is brought into contact with the exterior barrel 21 made of metal.

(Modification)

The endoscope 1 and the image pickup unit 30 according to the embodiment may be formed as various modifications described hereinafter.

(First Modification)

Figure 16:
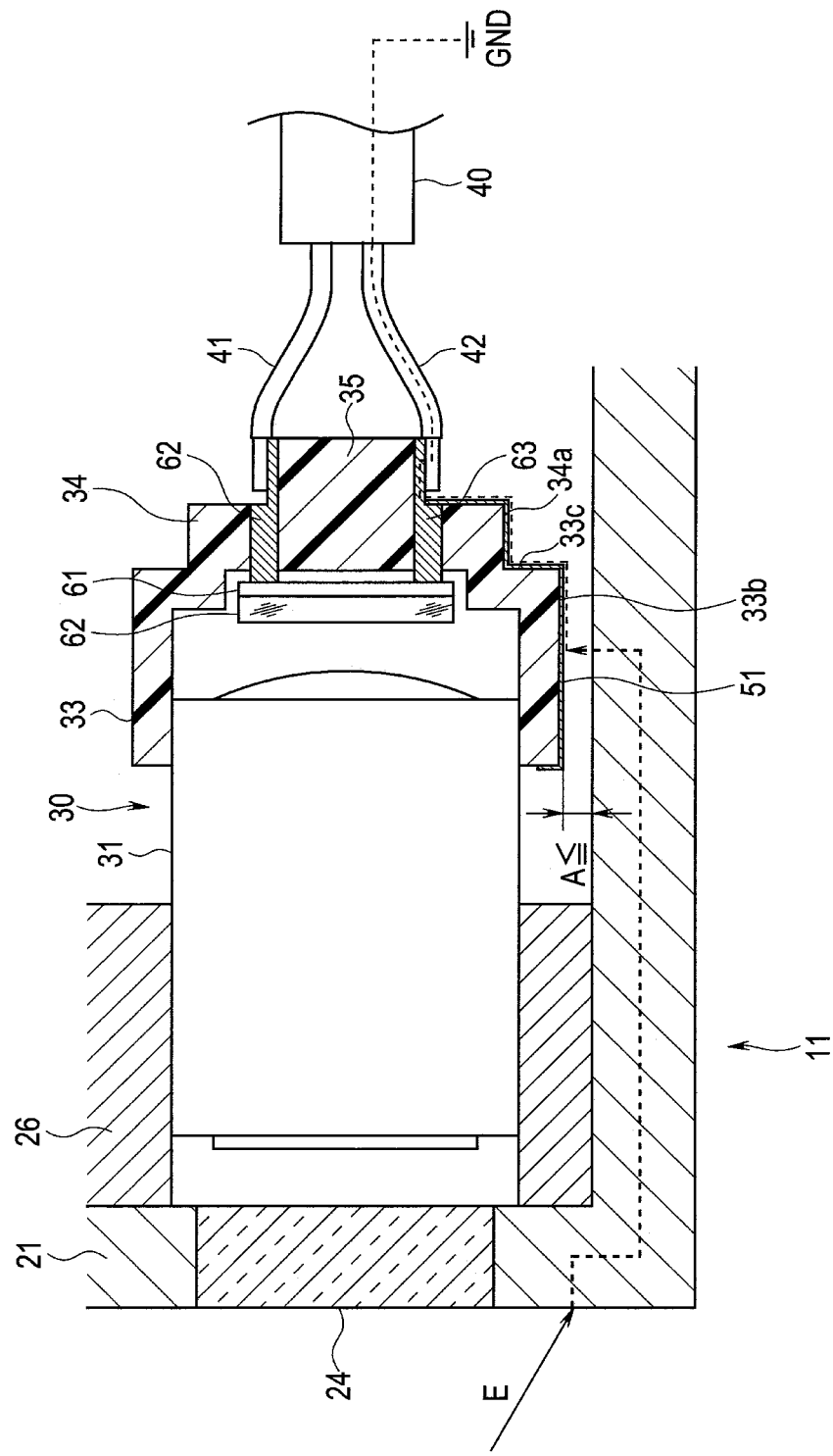
FIG. 16 is a partial cross-sectional view of a distal end portion on which an image pickup unit is mounted provided for describing a state where a current such as a high frequency current or static electricity is applied in a first modification of the endoscope.

FIG. 16 is a partial cross-sectional view of a distal end portion on which an image pickup unit is mounted provided for describing a state where a current such as a high frequency current or static electricity is applied in a first modification.

As shown in FIG. 16, an image pickup unit 30 can be mounted on a distal end portion 11 provided that a distance between an inner surface of an exterior barrel 21 and a metal PAD portion 51 formed on a substrate barrel 32 is a predetermined creepage distance A or more (A) which ensures insulation property, and by which a current E such as a leak current from high frequency treatment instrument or the like or static electricity between the metal PAD portion 51 and the exterior barrel 21 can be discharged.

(Second Modification)

Figure 17:
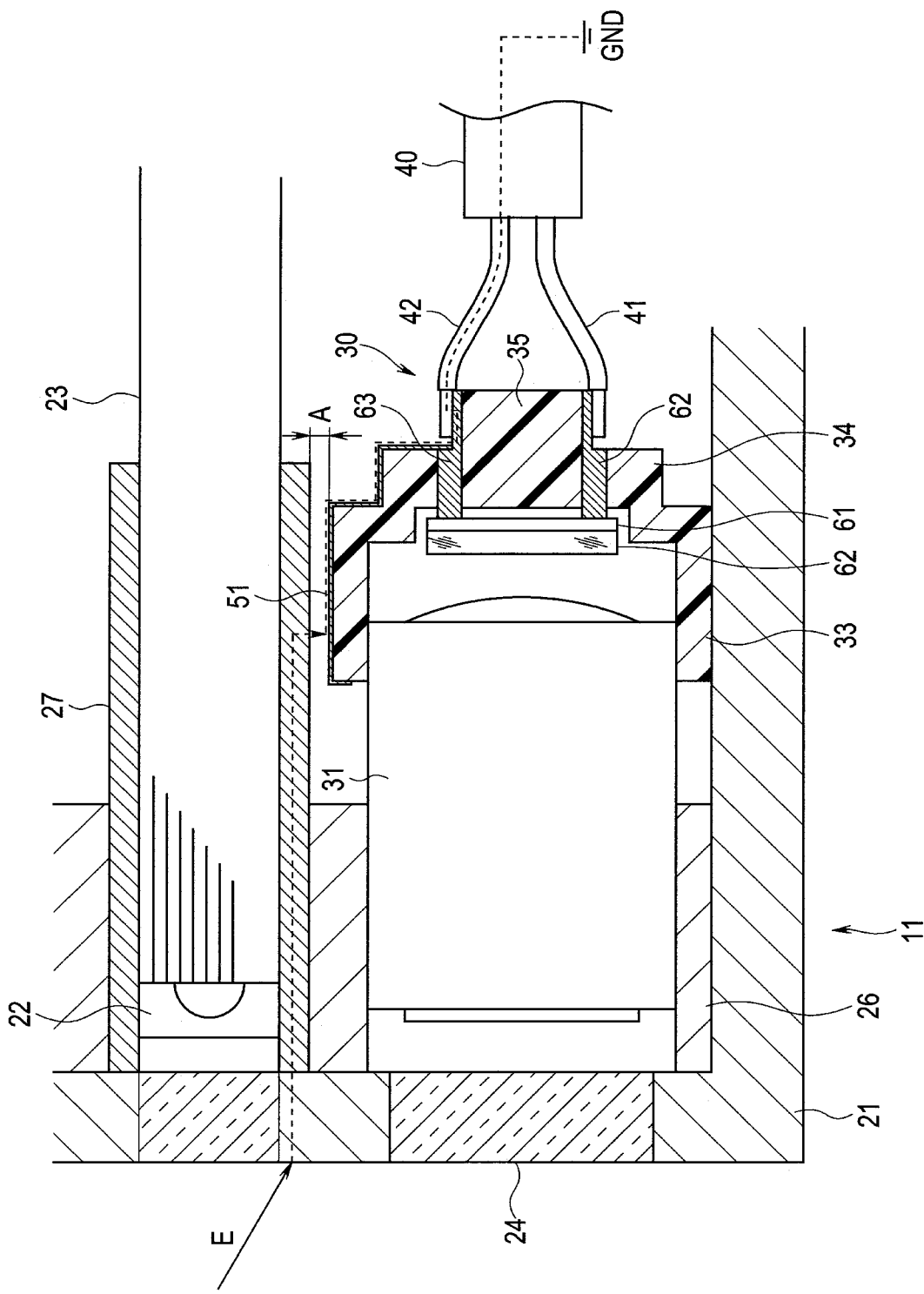
FIG. 17 is a partial cross-sectional view of a distal end portion on which an image pickup unit is mounted provided for describing a state where a current such as a high frequency current or static electricity is applied in a second modification of the endoscope.

FIG. 17 is a partial cross-sectional view of a distal end portion on which an image pickup unit is mounted provided for describing a state where a current such as a high frequency current or static electricity is applied in a second modification.

FIG. 17 shows a case where a hold tube 27 made of metal such as stainless steel which holds an illumination lens 22 and a light guide 23 is disposed on a distal end portion 11 of an endoscope 1. In this case, an image pickup unit 30 can be mounted on the distal end portion 11 such that a distance between an outer surface of the hold tube 27 and a metal PAD portion 51 formed on a substrate barrel 32 is a predetermined creepage distance A which ensures insulation property, and can discharge a current E such as a leak current from high frequency treatment instrument or the like or static electricity between the metal PAD portion 51 and the exterior barrel 21.

(Third Modification)

Figure 18:
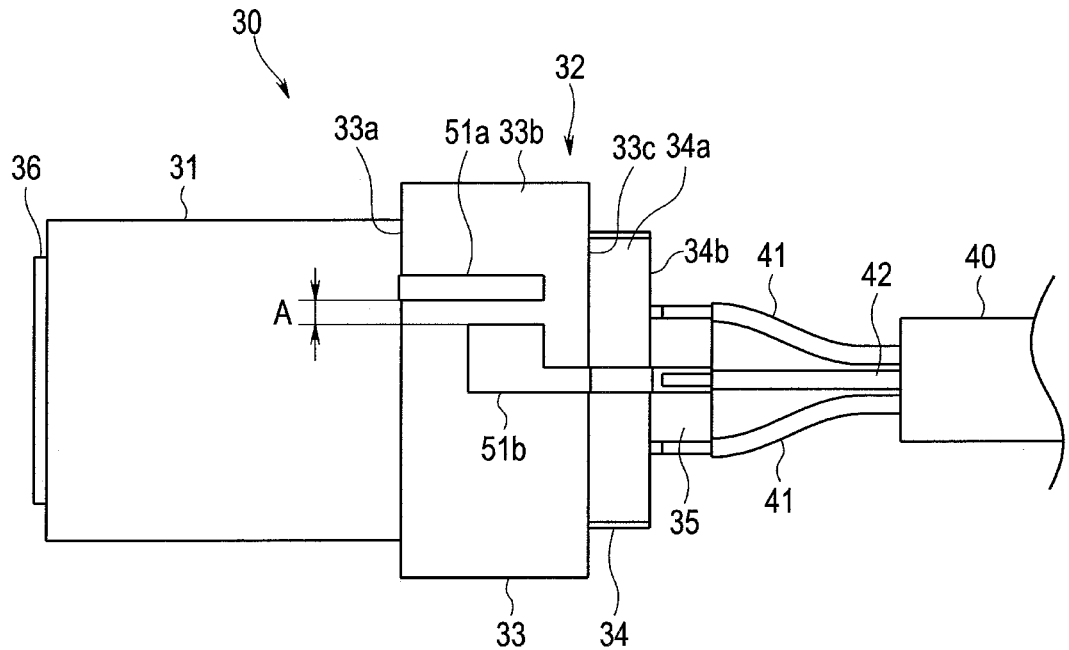
FIG. 18 is a top plan view showing a configuration of an image pickup unit according to a third modification of the endoscope.

FIG. 18 is a top plan view showing a configuration of an image pickup unit according to a third modification.

As shown in FIG. 18, in an image pickup unit 30, a plurality of metal PAD portions may be formed in a substrate barrel 32 in a split manner. In the modification, two metal PAD portions 51a, 51b are formed. The two metal PAD portions 51a, 51b are formed in the substrate barrel 32 such that a spaced-apart distance between the two metal PAD portions 51a, 51b forms a predetermined creepage distance A by which a current E such as a leak current from high frequency treatment instrument or the like or static electricity can be discharged.

In the configuration of the image pickup unit 30 according to the modification, an end portion of a lens hold barrel 31 and an end portion of the metal PAD portion 51a may be separated from each other by a predetermined creepage distance A or may be in contact with each other.

(Fourth Modification)

Figure 19:
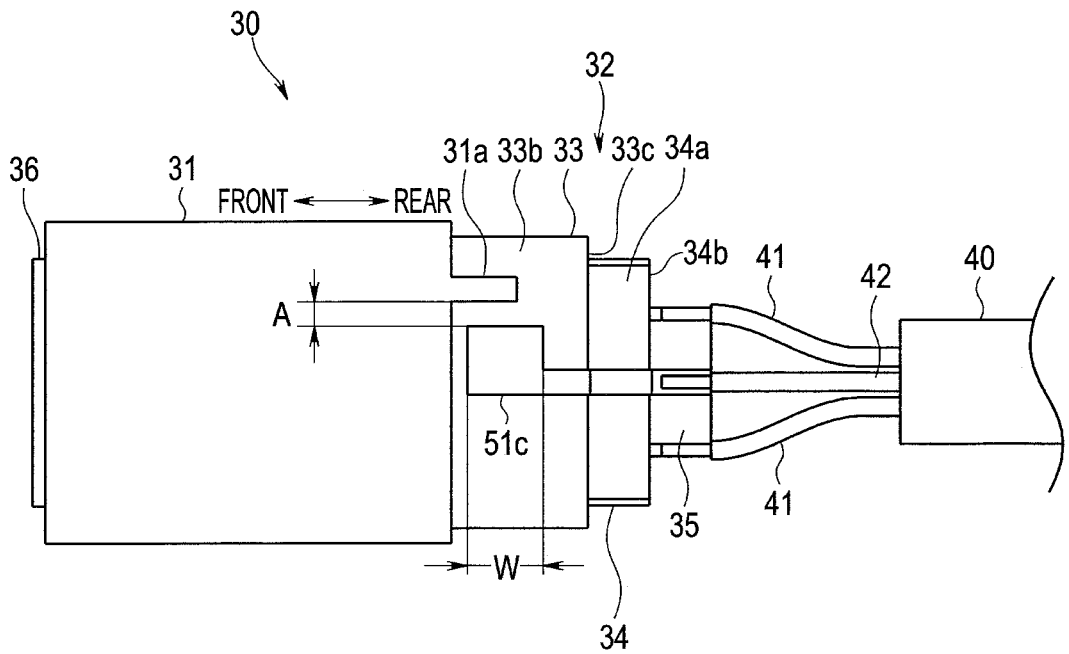
FIG. 19 is a top plan view showing a configuration of an image pickup unit according to a fourth modification of the endoscope.

FIG. 19 is a top plan view showing a configuration of an image pickup unit according to a fourth modification.

As shown in FIG. 19, in the modification, in an image pickup unit 30, a lens hold barrel 31 has a convex portion 31a extending toward a proximal end side, and the lens hold barrel 31 is fitted on a substrate barrel 32.

In the substrate barrel 32, the convex portion 31a of the lens hold barrel 31 is disposed on an outer surface, and a metal PAD portion 51c having a predetermined width (length) W is formed in an extending direction of the convex portion 31a. The convex portion 31a and the metal PAD portion are formed such that a spaced-apart distance between the convex portion 31a and the metal PAD portion forms a predetermined creepage distance A by which a current E such as a leak current from high frequency treatment instrument or the like or static electricity can be discharged.

The lens hold barrel 31 is moved with respect to the substrate barrel 32 in a longitudinal direction, and is fixed to the substrate barrel 32 at front and rear positions at which a predetermined optical performance (focus) is satisfied.

Accordingly, the metal PAD portion 51c is formed such that the metal PAD portion 51c has a predetermined width W which is equal to or more than a range (focusing adjustment amount) within which the position of the lens hold barrel 31 is adjusted so as to make the convex portion 31a never fail to overlap with the metal PAD portion 51c.

(Fifth Modification)

Figure 20:
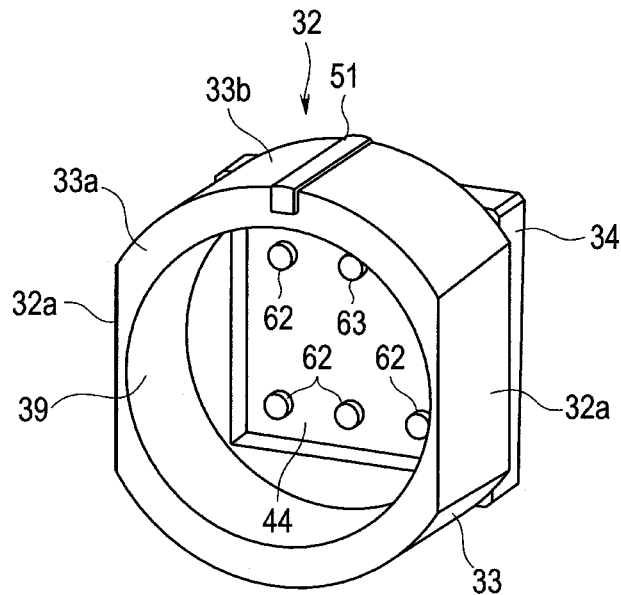
FIG. 20 is a perspective view of a substrate barrel according to a fifth modification of the endoscope as viewed from a distal end side.
Figure 21:
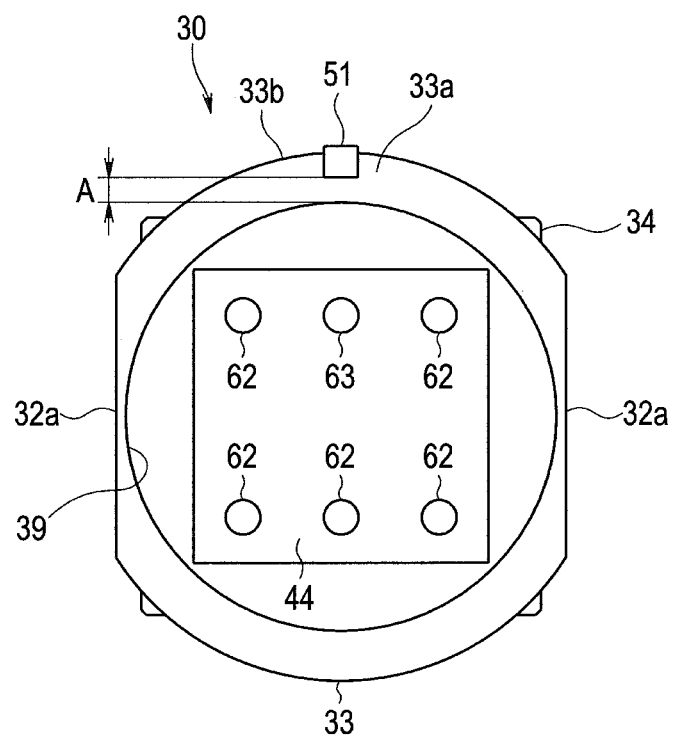
FIG. 21 is a front view showing a configuration of the substrate barrel according to the fifth modification of the endoscope.

FIG. 20 is a perspective view of a substrate barrel according to a fifth modification as viewed from a distal end side. FIG. 21 is a front view showing a configuration of the substrate barrel according to the fifth modification.

As shown in FIG. 20 and FIG. 21, a substrate barrel 32 may be miniaturized by forming a flat surface 32a on both respective side portions of a cylindrical portion 33. Provided that the substrate barrel 32 can maintain a strength, the flat surface 32a may be formed on the cylindrical portion 33 at a plurality of places so as to further miniaturize the substrate barrel 32.

The inventions described in the above-mentioned embodiment are not limited to the embodiment and the modifications, and various modifications can be carried out without departing from the gist of the present invention in a stage where the various modifications are carried out. Further, the above-mentioned embodiment contains the inventions in various stages, and various inventions can be extracted by suitably combining the plurality of components disclosed in the embodiment and the modifications.

For example, even when several components are deleted from the entire components described in the embodiment, in a case where stated tasks can be carried out and stated advantageous effects can be acquired, the configuration from which such components are deleted can be extracted as the invention.

According to the present invention, it is possible to provide an endoscope whose image pickup unit and distal end portion can be miniaturized while ensuring electric resistance from the outside.

What is claimed is:

1. An image pickup unit comprising:
a metal barrel disposed on a distal end side of the image pickup unit and holding an objective lens;
a substrate barrel fitted to a proximal end side of the metal barrel, the substrate barrel having an insulation property;
an image sensor disposed in the substrate barrel;
a plurality of electrodes penetrating the substrate barrel from an inside of the substrate barrel to a proximal end side of the substrate barrel, the plurality of electrodes being exposed on the inside of the substrate barrel to electrically connect the plurality of electrodes to the image sensor;
a first electric conductive member formed on an outer surface of the substrate barrel;
a ground electrode electrically connected to the first electric conductive member; and
a second electric conductive member extending from a proximal end side of the metal barrel, the second electric conductive member being disposed on the substrate barrel, the second electric conductive member being spaced apart from the first electric conductive member by a creepage distance, wherein
the creepage distance is such that the substrate barrel provides electrical insulation between the first and second electric conductive members during operation of the image sensor and enables discharge of an unintended outside current between the first and second electric conductive members.

2. The image pickup unit according to claim 1, wherein an insulation distance is provided between the first electric conductive member and the image sensor.

3. An endoscope comprising:
a distal end portion comprising an image pickup unit, wherein the image pickup unit comprising:
a metal barrel holding an objective lens;
a substrate barrel fitted to a proximal end side of the metal barrel, the substrate barrel having an insulation property;
an image sensor disposed in the substrate barrel;
a plurality of electrodes penetrating the substrate barrel from an inside of the substrate barrel to a proximal end side of the substrate barrel, the plurality of electrodes being exposed on the inside of the substrate barrel to electrically connect the plurality of electrodes to the image sensor;
a first electric conductive member formed on an outer surface of the substrate barrel;
a ground electrode electrically connected to the first electric conductive member;
a second electric conductive member extending from a proximal end side of the metal barrel, the second electric conductive member being disposed on the substrate barrel, the second electric conductive member being spaced apart from the first electric conductive member by a first creepage distance;
a cable including a ground wire connected to the ground electrode and a plurality of wires connected to the plurality of electrodes; and
wherein the first creepage distance is such that the substrate barrel provides electrical insulation between the first and second electric conductive members during operation of the image sensor and enables discharge of an unintended outside current between the first and second electric conductive members;
the first electric conductive member is spaced apart from the imaging sensor; and
the first electric conductive member overlaps with the second electric conductive member in a longitudinal direction.

4. The endoscope according to claim 3, further comprising a hold tube made of metal which holds a light guide,
wherein the first electric conductive member has a second creepage distance relative to the hold tube; and
the second creepage distance is such that the substrate barrel provides electrical insulation between the first electric conductive member and the hold tube during operation of the image sensor and enables discharge of an unintended outside current between the first electric conductive member and the hold tube.

5. The image pickup unit according to claim 1, wherein the second electric conductive member is spaced apart from the first electric conductive member at the creepage distance so that the second electric conductive member is configured to discharge at least one of a leak current and a static electricity from the first electric conductive member to the second electric conductive member.

6. The image pickup unit according to claim 1, wherein the second electric conductive member extends from the proximal end side of the metal barrel.

7. The image pickup unit according to claim 1, wherein the substrate barrel comprises a tubular portion connected to the metal barrel.

8. The image pickup unit according to claim 1, wherein the substrate barrel comprises:
a tubular portion connected to the metal barrel; and
a block portion formed on a proximal surface of the tubular portion, the block portion configured to close a proximal opening of the tubular portion.

9. The image pickup unit according to claim 1, wherein the substrate barrel comprises:
   a tubular portion connected to the metal barrel;
   a block portion formed on a proximal surface of the tubular portion, the block portion configured to close a proximal opening of the tubular portion; and
   a wiring portion formed on a proximal surface of the block portion.

10. The image pickup unit according to claim 9, wherein the block portion has a rectangular shape.

11. The image pickup unit according to claim 9, wherein the wiring portion has a rectangular shape.

12. The image pickup unit according to claim 9, wherein the first electric conductive member extends from an outer side surface of the tubular portion through the proximal surface of the tubular portion, to an outer side surface of the block portion, and from the proximal surface of the block portion to the ground electrode.

13. The image pickup unit according to claim 9, wherein the plurality of electrodes penetrate the block portion from a distal surface of the block portion to the proximal surface of the block portion.

14. The image pickup unit according to claim 9, wherein the ground electrode penetrates the block portion from a distal surface of the block portion to the proximal surface of the block portion.

15. The image pickup unit according to claim 13, wherein the ground electrode penetrates the block portion from a distal surface of the block portion to the proximal surface of the block portion.

16. The image pickup unit according to claim 3, wherein the second electric conductive member is spaced apart from the first electric conductive member at the first creepage distance so that the second electric conductive member is configured to discharge at least one of a leak current and a static electricity from the first electric conductive member to the second electric conductive member.

17. The endoscope according to claim 3, wherein the second electric conductive member extends from the proximal end side of the metal barrel.

18. The endoscope according to claim 3, wherein the substrate barrel comprises a tubular portion connected to the metal barrel.

19. The endoscope according to claim 3, wherein the substrate barrel comprises:
   a tubular portion connected to the metal barrel; and
   a block portion formed on a proximal surface of the tubular portion, the block portion configured to close a proximal opening of the tubular portion.

20. The endoscope according to claim 3, wherein the substrate barrel comprises:
   a tubular portion connected to the metal barrel;
   a block portion formed on a proximal surface of the tubular portion, the block portion configured to close a proximal opening of the tubular portion; and
   a wiring portion formed on a proximal surface of the block portion.

21. The image pickup unit according to claim 1, wherein
   the first electric conductive member is spaced apart from the imaging sensor, and
   the first electric conductive member overlaps with the second electric conductive member in a longitudinal direction.

\* \* \* \* \*